United States Patent [19]

Berg

[11] Patent Number: 5,772,853
[45] Date of Patent: Jun. 30, 1998

[54] SEPARATION OF 1-PROPANOL FROM T-AMYL ALCOHOL BY EXTRACTIVE DISTILLATION

[76] Inventor: Lloyd Berg, 1314 S. 3rd Ave., Bozeman, Mont. 59715

[21] Appl. No.: 971,290

[22] Filed: Nov. 17, 1997

[51] Int. Cl.$^6$ .............................. B01D 3/40; C07C 29/84
[52] U.S. Cl. ............................... 203/57; 203/58; 203/60; 203/62; 203/63; 203/64; 203/65; 203/69; 203/68; 203/70; 568/913
[58] Field of Search ................... 203/57–58, 60, 203/62–64, 65, 69–70, 68; 568/913

[56] References Cited

U.S. PATENT DOCUMENTS

| | | | |
|---|---|---|---|
| 1,862,706 | 6/1932 | Ricard et al. ............................ | 203/16 |
| 2,483,246 | 9/1949 | Stribley .................................. | 203/60 |
| 2,559,519 | 7/1951 | Smith et al. ............................ | 203/64 |
| 2,570,205 | 10/1951 | Carlson et al. ......................... | 203/58 |
| 2,595,805 | 5/1952 | Morrell et al. .......................... | 203/84 |
| 4,366,032 | 12/1982 | Mikitenko et al. ..................... | 203/58 |
| 4,693,787 | 9/1987 | Berg et al. .............................. | 203/57 |
| 4,935,103 | 6/1990 | Berg et al. .............................. | 203/60 |
| 5,718,809 | 2/1998 | Berg ....................................... | 203/57 |

*Primary Examiner*—Virginia Manoharan

[57] ABSTRACT

1-Propanol and t-amyl alcohol cannot be separated by distillation or rectification because of the closeness of their boiling points. 1-Propanol is readily separated from t-amyl alcohol by extractive distillation. Effective agents are dipentene, amyl acetate and 1,4-dioxane.

1 Claim, No Drawings

SEPARATION OF 1-PROPANOL FROM T-AMYL ALCOHOL BY EXTRACTIVE DISTILLATION

FIELD OF THE INVENTION

This invention relates to a method for separating 1-propanol from t-amyl alcohol using certain organic compounds as the agent in extractive distillation.

DESCRIPTION OF PRIOR ART

Extractive distillation is the method of separating close boiling compounds from each other by carrying out the distillation in a multiplate rectification column in the presence of an added liquid or liquid mixture, said liquid(s) having a boiling point higher than the compounds being separated. The extractive agent is introduced near the top of the column and flows downward until it reaches the stillpot or reboiler. Its presence on each plate of the rectification column alters the relative volatility of the close boiling compounds in a direction to make the separation on each plate greater and thus require either fewer plates to effect the same separation or make possible a greater degree of separation with the same number of plates. The extractive agent should boil higher than any of the close boiling liquids being separated and not form minimum azeotropes with them. Usually the extractive agent is introduced a few plates from the top of the column to insure that none of the extractive agent is carried over with the lowest boiling component. This usually requires that the extractive agent boil about twenty Celcius degrees or more higher than the highest boiling component.

At the bottom of a continuous column, the less volatile components of the close boiling mixtures and the extractive agent are continuously removed from the column. The usual methods of separation of these two components are the use of another rectification column, cooling and phase separation, or solvent extraction.

The usual method of evaluating the effectiveness of extractive distillation agents is the change in relative volatility of the compounds to be separated. Table 1 shows the degree of separation or purity obtainable by theoretical plates at several relative volatilities. Table 1 shows that a relative volatility of at least 1.2 is required to get an effective separation by rectification.

TABLE 1

Effect of Relative Volatility on Theoretical stage Requirements.

| Separation Purity, | Relative Volatility | | | | | | | |
|---|---|---|---|---|---|---|---|---|
| Both Products (Mole Fraction) | 1.02 | 1.1 | 1.2 | 1.3 | 1.4 | 1.5 | 2.0 | 3.0 |
| | Theoretical Stages at Total Reflux | | | | | | | |
| 0.999 | 697 | 144 | 75 | 52 | 40 | 33 | 19 | 12 |
| 0.995 | 534 | 110 | 57 | 39 | 30 | 25 | 14 | 9 |
| 0.990 | 463 | 95 | 49 | 34 | 26 | 22 | 12 | 7 |
| 0.98 | 392 | 81 | 42 | 29 | 22 | 18 | 10 | 6 |
| 0.95 | 296 | 61 | 31 | 21 | 16 | 14 | 8 | 4 |
| 0.90 | 221 | 45 | 23 | 16 | 12 | 10 | 5 | 3 |

1-Propanol and t-amyl alcohol boil five degrees apart and have a relative volatility of 1.15 which makes it difficult to separate them by conventional distillation or rectification. Table 2 shows that with an agent giving a relative volatility of 1.6, only twenty-seven actual plates are required to get 99% purity compared to 88 plates for straight rectification.

TABLE 2

Theoretical And Actual Plates Required vs. Relative Volatility for 1-Propanol From t-Amyl Alcohol

| Relative Volatility | Theoretical Plates Required At Total Reflux, 99% Purity | Actual Plates Required, 75% Purity |
|---|---|---|
| 1.15 | 66 | 88 |
| 1.4 | 26 | 35 |
| 1.5 | 22 | 30 |
| 1.6 | 20 | 27 |

OBJECTIVE OF THE INVENTION

The object of this invention is to Provide a process or method of extractive distillation that will enhance the relative volatility of 1-propanol and t-amyl alcohol in their separation in a rectification column. It is a further object of this invention to identify effective extractive distillation agents that are stable and can be recycled.

SUMMARY OF THE INVENTION

The objects of this invention are provided by a process for the separation of 1-propanol and t-amyl alcohol which entails the use of certain organic compounds when employed as the agent in extractive distillation.

DETAILED DESCRIPTION OF THE INVENTION

I have discovered that certain organic compounds will effectively increase the relative volatility between 1-propanol and t-amyl alcohol during rectification when employed as the agent in extractive distillation. They are butyl acetate, amyl acetate, hexyl acetate, benzyl acetate, hexyl formate, isobutyl isobutyrate, isobutyl butyrate, butyl butyrate, ethyl acotoacetate, dimethyl adipate, ethyl salicylate, dibutyl phthalate, butyl propionate, pentyl propionate, isopropyl palmitate, 2-heptanone, cyclopentanone, 3-heptanone, acetophenone, 2,6-dimethyl-4-heptanone, propylene glycol propyl ether, 2-ethoxyethanol, diethylene glycol, tripropylene glycol, 5-methyl-2-hexanone, o-xylene, 2-pentanone, decalin, dipentene, p-xylene, 1,2,3,4- tetrahydronaphthalene, nonane, diethylbenzene, dodecane, beta-pinene, phenyl ether, butyl ether, 1-methoxy-2-propanol, myrcene, anisole, N,N-dimethyl aniline, morpholine, pyridine, 4-methyl morpholine, 2-nitrotoluene, 3-nitrotoluene, nitrobenzene, butyronitrile, salicylaldehyde, 1,4-dioxane, 3-ethyl phenol, tetraethyl orthosilicate, 2-nitropropane, nonyl phenol, ethylbenzene, m-xylene, p-xylene and toluene.

TABLE 3

Effective Extractive Pistillation Agents For Separating 1-Propanol From t-Amyl Alcohol

| Compounds | Relative Volatility |
|---|---|
| None | 1.15 |
| Butyl acetate | 1.55 |
| Amyl acetate | 1.9 |
| Hexyl acetate | 1.3 |
| Benzyl acetate | 1.5 |
| Hexyl formate | 1.35 |
| Isobutyl isobutyrate | 1.3 |
| Isobutyl butyrate | 1.4 |

TABLE 3-continued

Effective Extractive Pistillation Agents For
Separating 1-Propanol From t-Amyl Alcohol

| Compounds | Relative Volatility |
|---|---|
| Butyl butyrate | 1.3 |
| Ethyl acetoacetate | 2.0 |
| Dimethyl adipate | 1.4 |
| Ethyl salicylate | 1.65 |
| Dibutyl phthalate | 1.35 |
| Butyl propionate | 1.35 |
| Pentyl propionate | 1.7 |
| Isopropyl palmitate | 1.45 |
| 2-Heptanone | 1.45 |
| Cyclopentanone | 1.55 |
| 3-Heptanone | 1.5 |
| 2,6-Dimethyl-4-heptanone | 1.4 |
| Acetophenone | 1.35 |
| Propylene glycol propyl ether | 1.7 |
| 2-Ethoxyethanol | 1.4 |
| Diethylene glycol | 1.3 |
| Tripropylene glycol | 1.3 |
| 5-Methyl-2-hexanone | 1.65 |
| o-Xylene | 1.7 |
| 2-Pentanone | 1.4 |
| Decalin | 1.3 |
| Dipentene | 1.6 |
| p-Xylene | 1.4 |
| 1,2,3,4-Tetrahydronaphthalene | 1.5 |
| Nonane | 1.6 |
| Diethylbenzene | 1.6 |
| Dodecane | 1.45 |
| Beta pinene | 1.45 |
| Phenyl ether | 1.35 |
| 1-Methoxy-2-propanol | 1.45 |
| Butyl ether | 1.8 |
| Myrcene | 1.65 |
| Anisole | 1.65 |
| N,N-dimethyl aniline | 1.7 |
| Morpholine | 1.3 |
| Pyridine | 1.45 |
| 4-Methyl morpholine | 1.45 |
| 2-Nitrotoluene | 1.4 |
| 3-Nitrotoluene | 1.5 |
| Nitrobenzene | 1.35 |
| Butyronitrile | 1.35 |
| Salicylaldehyde | 1.35 |
| 1,4-Dioxane | 1.55 |
| Tetraethylorthosilicate | 1.55 |
| 3-Ethyl phenol | 1.35 |
| 2-Nitropropane | 1.45 |
| Nonyl phenol | 1.3 |
| Ethyl benzene | 1.6 |
| m-Xylene | 1.6 |
| Toluene | 1.55 |
| p-Xylene | 1.7 |

THE USEFULNESS OF THE INVENTION

The usefulness of this invention can be demonstrated by referring to the data presented in Tables 1, 2 and 3. All of the successful agents show that 1-propanol can be separated from t-amyl alcohol by means of extractive distillation in a rectification column and that the ease of separation as measured by relative volatility is considerable.

WORKING EXAMPLE

1. Fifty grams of 1-propanol-t-amyl alcohol mixture and fifty grams of dipentene were charged to a vapor-liquid equilibrium still and refluxed for two hours. The vapor composition was 74.4 %1-propanol and 25.6% t-amyl alcohol. The liquid composition was 64.5% 1-propanol and 35.5% t-amyl alcohol. This is a relative volatility of 1.6.

I claim:

1. A method for recovering 1-propanol from a mixture consisting of 1-propanol and t-amyl alcohol which consists essentially of distilling a mixture consisting of 1-propanol and t-amyl alcohol in the presence of an extractive distillation agent, recovering the 1-propanol as overhead product and obtaining the t-amyl alcohol and the extractive distillation agent as bottoms product, wherein said extractive distillation agent consists essentially of one material selected from the group consisting of butyl acetate, amyl acetate, hexyl acetate, benzyl acetate, hexyl formate, isobutyl isobutyrate, isobutyl butryate, butyl butyrate, ethyl acetoacetate, dimethyl adipate, ethyl salicylate, dibutyl phthalate, butyl propionate, pentyl propionate, isopropyl palmitate, 2-heptanone, cyclepentanone, 3-heptanone, acetophenone, 2,6-dimethyl-4-heptanone, propylene glycol propyl ether, 2-ethoxyethanol, diethylene glycol, tripropylene glycol, 5-methyl-2-hexanone, o-xylene, 2-pentanone, decalin, dipentene, p-xylene, 1,2,3,4-tetrahydronaphthalene, nonane, diethylbenzene, dodecane, beta-pinene, phenyl ether, butyl ether, 1-methoxy-2-propanol, myrcene, anisole, N,N-dimethyl aniline, morpholine, pyridine, 4-methyl morpholine, 2-nitrotoluene, 3-nitrotoluene, nitrobenzene, butyronitrile, salicylaldehyde, 1,4-dioxane, 3-ethyl phenol, tetraethyl orthosilicate, 2-nitropropane, nonyl phenol, ethylbenzene, m-xylene, p-xylene and toluene.

* * * * *